United States Patent [19]

Lavielle et al.

[11] Patent Number: 4,885,299
[45] Date of Patent: Dec. 5, 1989

[54] 2-(2,3-DIHYDRO-2-OXO-3-BENZOFURANYL)ACETIC ACIDS HAVING ANTIHYPOXIC AND NOOTROPIC EFFECTS

[75] Inventors: Gilbert Lavielle, La Celle Saint-Cloud; Jean Lepagnol, Chatou, both of France

[73] Assignee: ADIR Et Cie, Neuilly-sur-Seine, France

[21] Appl. No.: 298,107

[22] Filed: Jan. 17, 1989

Related U.S. Application Data

[62] Division of Ser. No. 155,352, Feb. 12, 1988.

[30] Foreign Application Priority Data

Feb. 27, 1987 [FR] France ............... 87 02630

[51] Int. Cl.$^4$ .................. A61K 31/495; A61K 31/44; C07D 401/14; C07D 405/12
[52] U.S. Cl. ..................... 514/253; 514/233.5; 514/307; 514/310; 514/320; 514/397; 514/470; 544/153; 544/360; 544/364; 544/376; 544/377; 546/140; 546/146; 546/196; 548/336; 548/525; 549/407; 549/466
[58] Field of Search .............. 544/360, 364, 376, 377; 514/253

[56] References Cited

U.S. PATENT DOCUMENTS 2,513,698 7/1950 Weston et al. .................. 549/299

OTHER PUBLICATIONS

Lavielle et al., Chem. Abst. 110-75296z (1989).
Weston et al., Chem. Abst.; vol. 44, 8956a (1950) "2(3)-benzofuranone derivatives".

Primary Examiner—Cecilia Shen
Attorney, Agent, or Firm—Gordon W. Hueschen

[57] ABSTRACT

The invention relates to new 2-(2,3-dihydro-2-oxo-3-benzofuranyl)acetic acid compounds of general formula I:

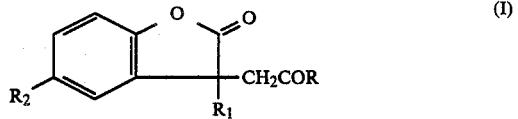

in which:
$R_1$ denotes a hydrogen atom, a linear or branched alkyl radical having 1 to 4 carbon atoms or a phenyl radical optionally substituted with a halogen atom or with an alkoxy radical containing 1 to 4 carbon atoms or an alkyl radical having 1 to 4 carbon atoms,
$R_2$ denotes a hydrogen or halogen atom, a hydroxyl radical, an alkyl radical having 1 to 4 carbon atoms or an alkoxy radical containing 1 to 4 carbon atoms,
R denotes a hydroxyl radical, a linear or branched alkoxy radical having 1 to 4 carbon atoms, a benzyloxy radical or a radical of general formula A:

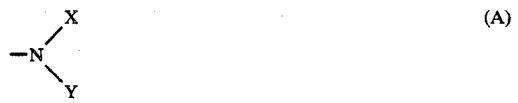

in which: X and Y, which may be identical or different, each denote a linear or branched alkyl radical containing 1 to 5 carbon atoms, a radical of general formula $A_1$ (CHZ—COOH)—, in which Z denotes a hydrogen atom, a linear or branched alkyl radical having 1 to 4 carbon atoms, a hydroxyalkyl radical having 1 to 4 carbon atoms, a 4-imidazolylmethylene radical or a benzyl radical optionally substituted with an alkyl radical having 1 to 4 carbon atoms or with a hydroxyl radical; a radical of general formula $A_2$ (CH$_2$W)—in which W denotes a linear or branched dialkylaminomethylene radical having 3 to 9 carbon atoms, a 2-pyrrolidinyl radical optionally substituted with an alkyl radical having 1 to 4 carbon atoms, a benzyl radical, a 1-isochromanyl radical or a 1-isoquinolyl radical, or form, together with the nitrogen to which they are attached, a 2-carboxy-2-pyrrolidinyl radical, a 4-morpholinyl radical, a piperidino radical optionally substituted with a phenyl radical or with an alkoxyphenyl radical having 7 to 10 carbon atoms, or a 1-piperazinly radical.

8 Claims, No Drawings

2-(2,3-DIHYDRO-2-OXO-3-BENZOFURANYL)ACETIC ACIDS HAVING ANTIHYPOXIC AND NOOTROPIC EFFECTS

This is a divisional of application Ser. No. 155,352, filed Feb. 12, 1988, pending.

The present invention relates to new 2-(2,3-dihydro-2-oxo-3-benzofuranyl)acetic acid compounds, processes for preparing them and the pharmaceutical compositions which contain them.

Surprisingly, few pharmacologically active 2,3-dihydro-2-oxobenzofuran compounds are mentioned in the literature. A few 3-aminoalkyl-2,3-dihydro-2-oxobenzofuran derivatives endowed with antispasmodic and local anesthetic activity are described in U.S. Pat. No. 2,513,698.

The Applicant has now discovered that certain 2-(2,3-dihydro-2-oxo-3-benzofuranyl)acetic acid compounds possess very advantageous pharmacological properties. In effect, the compounds of the present invention exert antihypoxic and nootropic effects without producing vascular effects. They significantly counteract brain death and tissue energy lack in the case of insufficiency of the oxygen supply, and find their application in the correction of disorders linked to hypoxemia and energy insufficiency, for example during cerebral aging.

The subject of the present invention is more especially 2-(2,3-dihydro-2-oxo-3-benzofuranyl)acetic acid compounds of general formula I

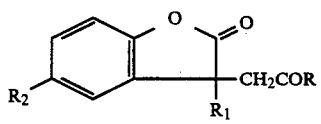

in which:

$R_1$ denotes a hydrogen atom, a linear or branched alkyl radical having 1 to 4 carbon atoms or a phenyl radical optionally substituted with a halogen atom or with an alkoxy radical containing 1 to 4 carbon atoms or an alkyl radical having 1 to 4 carbon atoms, $R_2$ denotes a hydrogen or halogen atom, a hydroxyl radical, an alkyl radical having 1 to 4 carbon atoms or an alkoxy radical containing 1 to 4 carbon atoms, R denotes either a hydroxyl radical, a linear or branched alkoxy radical having 1 to 4 carbon atoms or a benzyloxy radical or a radical of general formula A

in which X and Y, which may be identical or different, each denote a linear or branched alkyl radical containing 1 to 5 carbon atoms, a radical of general formula $A_1$

—CHZ—COOH  (A$_1$)

in which Z denotes a hydrogen atom, a linear or branched alkyl radical having 1 to 4 carbon atoms, a hydroxyalkyl radical having 1 to 4 carbon atoms, a 4-imidazolylmethylene radical or a benzyl radical optionally substituted with an alkyl radical having 1 to 4 carbon atoms or with a hydroxyl radical, a radical of general formula $A_2$

—CH$_2$W  (A$_2$)

in which W denotes a linear or branched dialkylaminomethylene radical having 3 to 9 carbon atoms, a 2-pyrrolidinyl radical optionally substituted with an alkyl radical having 1 to 4 carbon atoms, a benzyl radical, a 1-isochromanyl radical or a 1-isoquinolyl radical, • or form, together with the nitrogen to which they are attached, a 2-carboxy-2-pyrrolidinyl radical, a 4-morpholinyl radical, a piperidino radical optionally substituted with a phenyl radical or with an alkoxyphenyl radical having 7 to 10 carbon atoms, or a 1-piperazinyl radical (optionally substituted at the 4-position with a hydroxyalkyl radical having 1 to 4 carbon atoms, a carboxyalkyl radical having 2 to 5 carbon atoms, a benzyl radical optionally substituted with an alkyl radical having 1 to 4 carbon atoms, a 3,4-methylenedioxybenzyl radical, a phenyl radical optionally substituted with an alkyl radical having 1 to 4 carbon atoms or with a trifluoromethyl radical or with a halogen atom, or a 2-pyridyl radical optionally substituted with an alkyl radical having 1 to 4 carbon atoms or with a trifluoromethyl radical), in racemic form or in the form of optical isomers, and their addition salts with an inorganic or organic acid when they contain a salifiable basic group, or their addition salts with an inorganic or organic base when they contain a salifiable acidic group.

The subject of the present invention is also the process for preparing the compounds of general formula I, wherein a 2-benzofuranone of general formula II

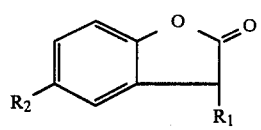

in which $R_1$ and $R_2$ have the meaning defined above for the formula I, is condensed with an alkyl or benzyl bromoacetate of general formula III —BrCH$_2$COR′  (III)

in which R′ denotes an alkoxy radical having 1 to 4 carbon atoms or a benzyloxy radical, to form a compound of general formula Ia

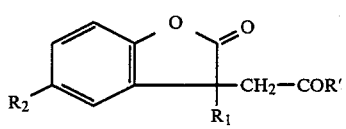

in which the definition of the substituents R′, $R_1$ and $R_2$ remains that stated above, then, wherein this compound can be subjected to a catalytic hydrogenation to obtain a 2-(2,3-dihydro-2-oxo-3-benzofuranyl)acetic acid compound of general formula Ib

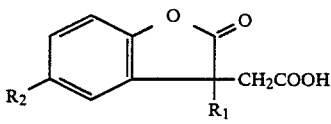

in which R₁ and R₂ have the meaning defined above, and then, to form the corresponding amides, wherein the latter compound is first subjected to the action of thionyl chloride to obtain an acyl halide of general formula IV

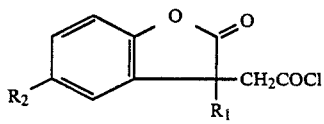

in which the definition of the substituents R₁ and R₂ remains that stated above, and wherein this is then condensed with a secondary amine of general formula V

in which X and Y have the meaning defined above for the formula I, to form the compounds of general formula Ic

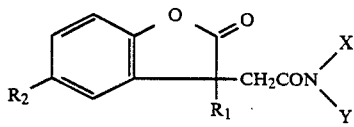

in which the meaning of the substituents R₁, R₂, X and Y remains identical to that given above.

The set of compounds of formulae Ia, Ib and Icforms the set of compounds of formula I, which, when they contain an acidic or basic group, can be salified, respectively, with a pharmaceutically acceptable inorganic or organic base or acid, or separated into their optical isomers and then optionally salified.

The 2-benzofuranones of general formula II, when they are not available commercially, may be prepared according to known processes [J. Med. Chem., (1972), 5, p. 551; U.S. Pat. No. 2,513,698 of 04.07.1950; Ber. (1897), 30, p. 124].

The condensation of the compounds of general formula II with alkyl or benzyl bromoacetates is performed in the presence of a metal hydride, such as sodium hydride, in an anhydrous organic solvent and at room temperature, according to known processes [J. Chem. Soc. (1973), p. 711; J. Org. Chem. (1961), 26, p. 4821].

The hydrogenolysis of the compounds of general formula Ia is performed in the presence of palladium on charcoal (10% palladium) at room temperature and at atmospheric pressure.

The condensation of the acid chlorides of general formula IV with the amines of general formula V is performed either in an anhydrous organic solvent such as benzene, or in alkaline aqueous medium when the compounds of general formula V are amino acids.

Among pharmaceutically acceptable acids for preparing the addition salts with the compounds of general formula I, hydrochloric, phosphoric, citric, oxalic, sulfuric, tartaric, maleic, mandelic and methanesulfonic acids, and the like, may be mentioned.

Among pharmaceutically acceptable bases for preparing the salts of the compounds of general formula I, sodium, potassium and ammonium hydroxides, and the like, may be mentioned.

The compounds according to the invention, as well as their salts, are endowed with highly advantageous pharmacological properties, and differ from the other 2,3-dihydro-2-oxobenzofuran compounds which are already known. In effect, in vivo pharmacological trials have shown that the compounds of the present invention exert a potent antihypoxic effect in animals.

During aging or as a consequence of a stroke, increased cell fragility and vulnerability are important physiopathological components, stimulating the search for new therapeutic agents directed towards protecting the brain, which is then placed in the position of being unable to respond to any further attack originating from its surroundings.

An attack of this kind may be repeated in the form of a deficiency in the oxygen supply, and for this reason, in respect of their consequences, there is a close analogy between hypoxia and cerebral aging. This analogy is expressed, in particular, by a fall in the energy reserves of the brain, a lower resistance to stress and a fall in the renewal of the oxygen-dependent synthesis of neurotransmitters.

The compounds of the present invention were tested in respect of their capacity to prolong the survival of cerebral tissue during acute hypoxia in mice, or to maintain the level of tissue energy-rich compounds in rats subjected to a fall in the oxygen supply [Pharmacology of Cerebral Ischemia, p. 334–339 (1968) Elsevier Science Publishers B.V., J. Krieglstein ed.]. In both types of experiment that were carried out, the compounds of the invention were compared with reference compounds, namely meclofenoxate, pyritinol and piracetam [Arz. Forsch. Drug. Res. (1986), 36 II No. 9, p. 1314–1320].

The latter were chosen on account of their therapeutic indications with respect to symptoms associated with senescence or to the sequelae of stroke, the indications being claimed on the basis of the antihypoxic and nootropic effect without the production of a vascular effect. Compounds of the myolitic or adrenolytic type were hence excluded.

The pharmacological trials in mice demonstrated that the compounds of the present invention have an antihypoxic protective effect which is 2 to 8 times as potent as that of the most active reference compound. In rats subjected to hypoxia, the compounds of the invention exerted the same protective effects on cerebral energy as the reference compounds, but at doses 3- to 10-fold lower, and thus confirmed the great advantage of their use in therapy.

By significantly counteracting brain death and tissue energy lack in the case of insufficiency of the oxygen supply, the compounds of the present invention exert a pronounced antihypoxic effect and are hence useful in cases of acute, transitory or progressive ischemic syndromes localized in any part of the body, since they exert their pharmacological properties with respect to the lack of oxygenation which accompanies these accidents. Their pharmacological properties enable them to be applied in the correction of disorders linked to hypoxemia and to energy insufficiency, for example, during cerebral aging.

The invention also encompasses the pharmaceutical compositions containing as active principal at least one compound of general formula I or one of its salts with a pharmaceutically compatible inorganic or organic base or acid, in combination with one or more suitable inert excipients.

The pharmaceutical compositions thereby obtained are advantageously presented in various forms, such as, for example, tablets, dragees, gelatin capsules, sublingual tablets or other galenical preparations suitable for sublingual administration, suppositories, injectable solutions or solutions to be taken by mouth.

The dosage can vary widely depending on the patient's age and weight, the nature and severity of the condition and also the administration route.

The preferred administration route is the oral or parenteral route. Generally speaking, the unit dose will range between 0.5 and 300 mg, and the daily dosage usable in human therapy between 0.5 and 900 mg.

The examples which follow, given without implied limitation, illustrate the invention.

The melting points stated are measured according to the micro-Köfler technique. The infrared spectra are obtained with solutions of the products in Nujol. The proton nuclear magnetic resonance (NMR) spectra were recorded at 60 MHz. The spectral physical constants of the compounds of general formula I are shown in Table I.

EXAMPLE 1

2-(5-Chloro-2,3-dihydro-2-oxo-3-phenyl-3-benzofuranyl)acetic acid

Stage A:

2-(5-Chloro-2,3-dihydro-2-oxo-3-phenyl-3-benzofuranyl)acetic acid benzyl ester

A solution of 0.204 mol of 5-chloro-2,3-dihydro-2-oxo-3-phenylbenzofuran in 200 ml of anhydrous dimethylformamide is added to a suspension of 0.204 mol of sodium hydride in 100 ml of anhydrous dimethylformamide. The medium is maintained with stirring at room temperature for one hour, 0.224 mol of benzyl bromoacetate is then added slowly and the medium is left for 12 hours at room temperature. The reaction mixture is concentrated under vacuum and hydrolyzed using one liter of water, the aqueous phase extracted with twice 250 ml of benzene, the organic phase dried over anhydrous sodium sulfate and the solvent evaporated off. The residue is washed with isopropyl ether and then filtered. 0.173 mol is thereby obtained.

Yield: 85% .
Melting point: 95° C.

Stage B:

0.127 mol of the benzyl ester obtained in the above stage, 2 g of palladium on charcoal (10% palladium) and 700 ml of anhydrous ethanol are mixed in a 2-liter round-bottomed flask. The medium is hydrogenated at room temperature and at atmospheric pressure. When the requisite quantity of hydrogen has been absorbed, the catalyst is filtered off and the solvent evaporated off. The crystalline residue is washed with petroleum ether and 35 g of crystals are collected after filtration.

Yield: 90% .
Melting point: 199° C.

EXAMPLES 2 to 6:

The following compounds were prepared according to the process described in Example 1, using at Stage A the appropriate 2,3-dihydro-2-oxo-3-phenylbenzofuran derivatives.

EXAMPLE 2:

2-(2,3-Dihydro-5-fluoro-2-oxo-3-phenyl-3-benzofuranyl)acetic acid

Yield: 85% .
Melting point: 228° C.

EXAMPLE 3:

2-(2,3-Dihydro-2-oxo-3-phenyl-3-benzofuranyl) acetic acid

Yield: 95% .
Melting point: 184° C.

EXAMPLE 4:

2-[3-(4-Chlorophenyl)-2,3-dihydro-2-oxo-3-benzofuranyl)acetic acid

Yield: 90% .
Melting point: 192° C.

EXAMPLE 5:

2-(2,3-Dihydro-5-hydroxy-2-oxo-3-phenyl-3-benzofuranyl)acetic acid

Yield: 90% .
Melting point: 226° C.

EXAMPLE 6:

2-(2,3-Dihydro-5-methoxy-2-oxo-3-phenyl-3-benzofuranyl)acetic acid

Yield: 85% .
Melting point: 188° C.

EXAMPLE 7:

2-(2,3-Dihydro-5-hydroxy-3-oxo-3-phenyl-3-benzofuranyl)acetic acid benzyl ester

This compound was prepared from 2,3-dihydro-5-hydroxy-2-oxo-3-phenylbenzofuran according to the process described in Stage A in Example 1.

Yield: 33% .
Melting point: 96° C.

EXAMPLE 8:

2-(5-Chloro-2,3-dihydro-2-oxo-3-phenyl-3-benzofuranyl)acetic acid ethyl ester

A solution of 42.8 mmol of 5-chloro-2,3-dihydro-2-oxo-3-phenylbenzofuran in 50 ml of anhydrous dimethylformamide is added at room temperature to a suspension of 42.8 mmol of sodium hydride in 20 ml of anhydrous dimethylformamide. The mixture is stirred for one hour at 20° C. and 42.8 mmol of ethyl bromoacetate are added. The mixture is stirred for 12 hours at 20° C., the medium concentrated under vacuum, the residue taken up in 200 ml of 1% strength hydrochloric acid solution, the aqueous phase extracted with benzene, the organic phase dried over anhydrous sodium sulfate, the solvent evaporated off and the crystalline residue washed with a solution of ethyl ether and acetone (90:10). After filtration, 25.8 mmol of crystals are collected.
Yield: 60%.
Melting point: 130° C.

EXAMPLE 9:

2-(5-Chloro-2,3-dihydro-2-oxo-3-phenyl-3-benzofuranyl)-1-[4-(5-trifluoromethyl-2-pyridyl)-piperazinyl]-1-oxoethane Stage A 2-(5-Chloro-2,3-dihydro-2-oxo-3-phenyl-3-benzofuranyl)acetyl chloride 23.7 g of double-distilled thionyl chloride are added dropwise to a solution, stirred and heated to 70° C., of 30.2 g of 2-(5-chloro-2,3-dihydro-2-oxo-3-phenyl-3-benzofuranyl)acetic acid in 250 ml of anhydrous benzene. When the addition is complete, the mixture is heated to reflux until the evolution of gas has completely ceased. The medium is concentrated under vacuum, the residue washed with 200 ml of anhydrous benzene and the solvent evaporated off. This operation is repeated twice and the product is left to crystallize at room temperature. The crystals are washed with petroleum ether and filtered off, and 31 g of pure product are obtained.
Yield: 95%.
Melting point: 107° C.

Stage B

A solution of 7.5 g of 4-(3-trifluoromethyl-2-pyridyl)-piperazine and 3.15 g of triethylamine in 100 ml of anhydrous benzene is added to a solution, cooled beforehand to 6° C., of 10 g of acid chloride obtained in the above stage in 200 ml of anhydrous benzene. The mixture is stirred for 2 hours at 20° C. and concentrated under vacuum, the residue neutralized using 1N sodium hydroxide solution, the aqueous phase extracted twice using 200 ml of dichloromethane, the organic phase washed with water and dried over anhydrous sodium sulfate and the solvent evaporated off. The crude product is recrystallized in ethanol to obtain 5 g of product.
Yield: 30%.
Melting point: 228° C.

EXAMPLE 10

N,N-Diethyl-2-(5-chloro-2,3-dihydro-2-oxo-3-phenyl-3-benzofuranyl)acetamide

This compound was prepared according to the process described in Example 9, using diethylamine at Stage B.
Yield: 50%.
Melting point: 145° C.

EXAMPLE 11

N-Methyl-N-[2-(5-chloro-2,3-dihydro-2-oxo-3-phenyl-3-benzofuranyl)acetyl]leucine 0.9 g of sodium hydroxide is added to a solution of 3 g of N-methylleucine in 70 ml of water and 40 ml of tetrahydrofuran. The medium is then cooled to 5° C. and a solution of 7.3 g of 2-(5-chloro-2,3-dihydro-2-oxo-3-phenyl-3-benzofuranyl)acetyl chloride in 50 ml of tetrahydrofuran and a solution of 0.9 g of sodium hydroxide in 22.7 ml of water are then added simultaneously in small portions so as to maintain the pH at 12. The mixture is stirred for 3 hours at room temperature and 22.7 ml of N hydrochloric acid are added. The medium is concentrated and the precipitate obtained is filtered off and dissolved hot in an ethanol/methanol (50:50) mixture. The solution is filtered and the filtrate evaporated. A crystalline product is obtained.
Yield: 65%.
Melting point: 183° C.

EXAMPLE 12

N-Methyl-N-diethylaminoethyl-2-(5-chloro-2,3-dihydro-2-oxo-3-phenyl-3-benzofuranyl)acetamide hydrochloride This compound was prepared according o the process described in Example 9, using in Stage B N-methyl-N-diethylaminoethylamine and then salifying the product obtained with hydrochloric acid dissolved in ethanol.
Yield: 70%.
Melting point: 190° C.

EXAMPLE 13

N-[2-(5-chloro-2,3-dihydro-2-oxo-3-phenyl-3-benzofuranyl)acetyl]proline

This compound was prepared according to the process described in Example 11, using proline as the amino acid.
Yield: 65%.
Melting point: >260° C.

EXAMPLES 14-19

The following compounds were prepared according to the process described in Example 9, using the appropriate amines in Stage B.

EXAMPLE 14

2-(5-Chloro-2,3-dihydro-2-oxo-3-phenyl-3-benzofuranyl)-1-morpholino-1-oxoethane
Yield: 76%.
Melting point: 211° C.

EXAMPLE 15

2-(5-Chloro-2,3-dihydro-2-oxo-3-phenyl-3-benzofuranyl)-1-[4-(2-hydroxyethyl)piperazinyl]-1-oxoethane hydrochloride
Yield: 25%.
Melting point: 235° C.

EXAMPLE 16

2-(5-Chloro-2,3-dihydro-2-oxo-3-phenyl-3-benzofuranyl)-1-[4-(3,4-methylenedioxybenzyl)-piperazinyl]-1-oxoethane
Yield: 55%.
Melting point: >260° C.

EXAMPLE 17

2-(5-Chloro-2,3-dihydro-2-oxo-3-phenyl-3-benzofuranyl)-1-(4-benzylpiperazinyl)-1-oxoethane
Yield: 65%.
Melting point: 155° C.

EXAMPLE 18

2-(5-Chloro-2,3-dihydro-2-oxo-3-phenyl-3-benzofuranyl)-1-[4-(3-trifluoromethylphenyl)piperazinyl)-1-oxoethane hydrochloride
Yield: 90%.
Melting point: 192° C.

EXAMPLE 19

2-(5-Chloro-2,3-dihydro-2-oxo-3-phenyl-3-benzofuranyl)-1-[4-(3-methylphenyl)piperazinyl]-1oxoethane hydrochloride Yield: 40%.
Melting point: 261° C.

EXAMPLE 20

2-(5-Fluoro-2,3-dihydro-2-oxo-3-phenyl-3-benzofuranyl)-1-[4-(3,4-methylenedioxybenzyl)-piperazinyl]-1-oxoethane hydrochloride This compound was prepared according to the process described in Example 9, starting with 2-(5-fluoro-2,3-dihydro-2-oxo-3-phenyl-3-benzofuranyl)acetyl chloride and 4-(3,4-methylenedioxybenzyl)piperazine.
Yield: 45%.
Melting point: 195° C.

EXAMPLE 21

N-Methyl-N-[2-(2,3-dihydro-2-oxo-3-phenyl-3-benzofuranyl)acetyl]glycine

This compound was prepared according to the process described in Example 11, starting with 2-(2,3-dihydro-2-oxo-3-phenyl-3-benzofuranyl)acetyl chloride and N-methyl glycine.
Yield: 55%.
Melting point: 120° C.

EXAMPLE 22

2-(2,3-Dihydro-2-oxo-3-phenyl-3-benzofuranyl)-1-[4-(3,4-methylenedioxybenzyl)piperazinyl]-1-oxoethane hydrochloride This compound was prepared from 2-(2,3-dihydro-2-oxo-3-phenyl-3-benzofuranyl)acetyl chloride and 4-(3,4-methylenedioxybenzyl)piperazine according to the process described in Example 9.
Yield: 45%.
Melting point: 192° C.

EXAMPLE 23

2-(2,3-dihydro-2-oxo-3-benzofuranyl)1-[4-(3,4-methylenedioxybenzyl)piperazinyl]-1-oxoethane hydrochloride Stage A 2-(2,3-dihydro-2-oxo-3-benzofuranyl)acetic acid benzyl ester A mixture of 7.53 g of diisopropylamine in 150 ml of anhydrous tetrahydrofuran is cooled under a stream of nitrogen to −60° C. 46.6 ml of a 1.6M solution of n-butyl-lithium in hexane is added dropwise a this temperature. When the addition is complete, the temperature of the reaction medium is allowed to rise to 5° C., the mixture is stirred for 10 minutes at this temperature and cooled to −80° C. and a solution of 10 g of 2,3-dihydro-2-benzofuranone in 150ml of anhydrous tetrahydrofuran is added dropwise. The mixture is maintained for 10 minutes at −80° C. and then for 10 minutes at −60° C. It is cooled again to −80° C. and a solution of 18.8 g of benzyl bromoacetate in 16.05 g of hexamethylphosphorotriamide is added. The temperature is allowed to rise to 20° C., and the reaction mixture is stirred for 1 hour at this temperature and hydrolyzed at 0° C. using 26 ml of saturated ammonium chloride solution. The medium is then poured into 2.5 L of 1% strength hydrochloric acid solution. The precipitate is filtered off and dissolved in 200 ml of benzene, the organic phase is washed with water and dried over anhydrous sodium sulfate and the solvent is evaporated off. The residue is recrystallized in petroleum ether.
Yield: 90%.
Melting point: 88° C.

Stage B 2-(2,3-Dihydro-2-oxo-3-benzofuranyl)acetic acid

This acid is obtained from the compound synthesized in the above stage, according to the process described in Example 1, Stage B.

Stage C 2-(2,3-Dihydro-2-oxo-3-benzofuranyl)acetyl chloride

This compound was prepared according to the process described in Example 9, Stage A, starting with 2-(2,3-dihydro-2-oxo-3-benzofuranyl)acetic acid.

Stage D

A solution of 9.4 g of 4-(3,4-methylenedioxybenzyl)piperazine in 100 ml of anhydrous benzene is added to a solution, cooled beforehand to 10° C., of 4.5 g of 2-(2,3-dihydro-2-oxo-3-benzofuranyl)acetyl chloride in 50 ml of anhydrous benzene. The mixture is stirred for 12 hours at room temperature and the precipitate of amine hydrochloride is filtered off and washed several times with benzene. The combined organic phases are washed with water, dried over anhydrous sodium sulfate and concentrated under vacuum. The crude product obtained is chromatographed on 300 g of 70–230 mesh silica (eluant: dichloromethane/methanol 9.5:2.5 V/V). The resulting product (3g) is dissolved in the minimum amount of acetone and crystallized in the form of the hydrochloride by adding 1.5 ml of 5.07N ethanolic hydrochloric acid.
Yield: 35%.
Melting point: 188° C.

EXAMPLES 24–25

These compounds were prepared by condensing 2-(2,3-dihydro-2-oxo-3-benzofuranyl)acetyl chloride with the appropriate amines according to the process described in Example 23, Stage D.

EXAMPLE 24

2-(2,3-Dihydro-2-oxo-3-benzofuranyl)-1-morpholino-1-oxoethane

Yield: 50%
Melting point: 103° C.

EXAMPLE 25

2-(2,3-Dihydro-2-oxo-3-benzofuranyl)-1-[4-(3-methylbenzyl)piperazinyl]-1-oxoethane hydrochloride Yield: 50%.
Melting point: 138° C.

EXAMPLE 26

2-(5-Chloro-2,3-dihydro-2-oxo-3-benzofuranyl)-1-[4-(3-methylphenyl)piperazinyl]-1-oxoethane hydrochloride This compound was prepared according to the process described in Example 23, using 5-chloro-2,3-dihydro-2-benzofuranone in Stage A and 4-(3-methylphenyl)piperazine in Stage D.
Yield: 25%.
Melting point: 160° C.

EXAMPLE 27

2-(5-Chloro-2,3-dihydro-2-oxo-3-phenyl-3-benzofuranyl)-1-[4-(4-trifluoromethyl-2-pyridyl)-piperazinyl]-1-oxoethane This compound was prepared by condensing 2-(5-chloro-2,3-dihydro-2-oxo-3-phenyl-3-benzofuranyl)acetyl chloride with 2-(4-trifluoromethyl-2-pyridyl)piperazine according to the process described in Example 9, Stage B.
Yield: 40%.
Melting point: 202° C.

EXAMPLE 28

N-[2-(5-Chloro-2,3-dihydro-2-oxo-3-phenyl-3-benzofuranyl)acetyl]-N-methylphenylalanine This compound was prepared according to the process described in Example 11, using N-methylphenylalanine as amino acid.
Yield: 65%.
Melting point: 130–135° C.

EXAMPLE 29

2-(5-Chloro-2,3-dihydro-2-oxo-3-phenyl-3-benzofuranyl)-1-(4-carboxymethylpiperazinyl)-1-oxoethane hydrochloride This compound was prepared according to the process described in Example 11, using 2-piperazinylacetic acid as amino acid.
Yield: 80%.
Melting point: 224° C.

EXAMPLES 30–32

The compounds mentioned above were prepared by condensing 2-(5-chloro-2,3-dihydro-2-oxo-3-phenyl-3-benzofuranyl)-acetyl chloride with appropriate amines according to the process described in Example 9, Stage B.

EXAMPLE 30

2-(5-Chloro-2,3-dihydro-2-oxo-3-phenyl-3-benzofuranyl)-1-[3-(3-methoxyphenyl)piperidyl]-1-oxoethane Yield: 80%.
Melting point: 202° C.

EXAMPLE 31

2-(5-Chloro-2,3-dihydro-2-oxo-3-phenyl-3-benzofuranyl)-1-[N-(1-isochromanylmethyl)-N-methyl-]amino-1-oxoethane Yield: 70%.
Melting point: 159° C.

EXAMPLE 32

2-(5-Chloro-2-oxo-3-phenyl-3-benzofuranyl)-1-[(1-ethylpyrrolidinyl)methyl]methylamino-1-oxoethanehydrochloride Yield: 40%.
Melting point: 218° C.

EXAMPLE 33

2-(2,3-Dihydro-5-methyl-2oxo-3-phenyl-3-benzofuranyl)-1-[4-(4-fluorophenyl)piperazinyl]-1-oxoethane This compound was prepared by condensing 2-(2,3-dihydro-5-methyl-2-oxo-3-phenyl-3-benzofuranyl)acetyl chloride with 4-(4-fluorophenyl)piperazine according to the process described in Example 9, Stage B.
Yield: 82%.
Melting point: 120° C.

EXAMPLE 34

2-(2,3-Dihydro-2-oxo-3-propyl-3-benzofuranyl)-1-[4-(3,4-methylenedioxybenzyl)piperazinyl]-1-oxoethanehydrochloride Stage A (2,3-Dihydro-2-oxo-3-propyl-3-benzofuranyl)acetic acid benzyl ester A solution of 0.204 mol of 2,3-dihydro-2-oxo-3-propylbenzofuran in 200 ml of anhydrous dimethylformamide is added to a suspension of 0.204 mol of sodium hydride in 100 ml of anhydrous dimethylformamide. The medium is maintained with stirring at room temperature for one hour, 0.224 mol of benzyl bromoacetate is then added and the medium is left for 12 hours at room temperature. The reaction mixture is concentrated under vacuum and hydrolyzed using one liter of water, the aqueous phase is extracted with twice 250 ml of benzene, the organic phase dried over anhydrous sodium sulfate and the solvent evaporated off. The crystallized residue is washed with isopropyl ether and filtered, yielding 0.173 mol of a pale yellow oil.
Yield: 85%.

Stage B (2,3-Dihydro-2-oxo-3-propyl-3-benzofuranyl)acetic acid 50 g of the benzyl ester obtained in the above stage, 2 g of palladium on charcoal (10% palladium) and 700 ml of anhydrous ethanol are mixed in a 2 l round-bottomed flask. The medium is hydrogenated at room temperature and at atmospheric pressure. When the necessary quantity of hydrogen has been absorbed, the catalyst is filtered off and the solvent evaporated off. The crystalline residue is washed with petroleum ether and the crystals are collected after filtration.
Yield: 70%.
Melting point: 117° C.

Stage C 2-(2,3-Dihydro-2-oxo-3-propyl-3-benzofuranyl)acetyl chloride 23.7 g of double-distilled thionyl chloride are added dropwise to a solution, stirred and heated to 70° C., of 23.4 g of (2,3-dihydro-2-oxo-3-propyl-3-benzofuranyl)acetic acid in 250 ml of anhydrous benzene. When the addition is complete, the mixture is heated until the evolution of gas has completely ceased. The medium is concentrated under vacuum, the residue washed with 200 ml of anhydrous benzene and the solvent evaporated off. This operation is repeated twice, and a very thick oil which does not crystallize is obtained.
Yield: 95%.

Stage D

A solution of 6.85 g of 4-(3,4-methylenedioxybenzyl)-piperazine and 3.15 g of triethylamine in 100 ml of anhydrous benzene is added to a solution, cooled beforehand to 6° C., of 7.85 g (31.1 mmol) of the above acid chloride in 200 ml of anhydrous benzene. The mixture is stirred for 2 h at 20° C. and concentrated under vacuum, the residue taken up with benzene, the organic phase washed with water and dried over anhydrous sodium sulfate and the solvent evaporated off. The residue is recrystallized in a mixture of isopropyl ether and isopropyl alcohol (47:10). The crystals obtained are dissolved in ethanol and a sufficient quantity of a solution of hydrochloric acid in ethanol is added, the reaction medium is concentrated and ethyl is added to crystalize the hydrochloride formed.

Yield: 60%.
Melting point: 170°–175° C.

EXAMPLES 35–37

These compounds were prepared by condensing 2-[5-chloro-2,3-dihydro-2-oxo-3-(4-methylphenyl)-3-benzofuranyl]acetyl chloride with the appropriate amines.

EXAMPLE 35

N-Methyl-N-diethylaminoethyl-2-[5-chloro-2,3-dihydro-2-oxo-3-(4-methylphenyl)-3-benzofuranyl]acetamide hydrochloride Yield: 37%.
Melting point: 140° C.

EXAMPLE 36

N-Methyl-N-diisopropylaminoethyl-[5-chloro-2,3-dihydro-2-oxo-3-(4-methylphenyl)-3-benzofuranyl]acetamide hydrochloride Yield: 30%.
Melting point: 190° C.

EXAMPLE 37

2-[5-Chloro-2,3-dihydro-2-oxo-3-(4-methylphenyl)-3-benzofuranyl]-1-[4-(2-hydroethyl)piperazinyl]-1-oxoethane hydrochloride Yield: 33%.
Melting point: >260° C.

TABLE I

| Ex. | $R_1$ | R | $R_2$ | IR(cm$^{-1}$) $vC=0$ lactone | IR(cm$^{-1}$) $vC=0$ extracyclic | NMR (solvent) |
|---|---|---|---|---|---|---|
| 1 | 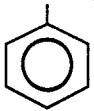 | —OH | —Cl | 1800 | 1705 | (CDCl$_3$ + DMSO—d$_6$) 9.2 ppm,m, exchangeable 1H 6.5 to 7.6 ppm,H; 3.4 ppm,AB,2H; |
| 2 | 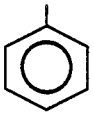 | —OH | —F | 1810 | 1715 | (CDCl$_3$ + DMSO—d$_6$) 9.75 ppm,m, exchangeable 1H 6.75 to 7.75 ppm,m,8H; 3.45 ppm,AB,2H |
| 3 | 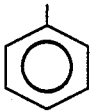 | —OH | —H | 1805 | 1715 | (CDCl$_3$ + DMSO—d$_6$) 10.3 ppm,m, exchangeable 1H 6.7 to 7.6 ppm,m,9H; 3.4 ppm,AB,2H |
| 4 | 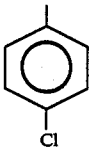 | —OH | —H | 1800 | 1710 | (DMSO—d$_6$) 12.5 ppm,m, exchangeable 1H 6.9 to 7.7 ppm,m,8H; 3.6 ppm,s,2H |
| 5 | 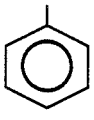 | —OH | —OH | 1785 | 1700 | (CDCl$_3$ + DMSO—d$_6$) 9.6 ppm,m, exchangeable 2H 7.3 ppm,s,5H; 6.6 to 7.2 ppm,m,3H; 3.4 ppm,AB,2H |
| 6 | 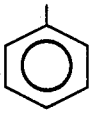 | —OH | —OCH$_3$ | 1800 | 1710 | (CDCl$_3$ + DMSO—d$_6$) 10.3 ppm,m, exchangeable 1H 7.3 ppm,s,5H; 6.6 to 7.2 ppm,m,3H; 3.8 ppm,s,3H; 3.4 ppm,AB,2H |
| 7 | 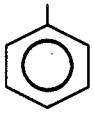 | —OCH$_2$—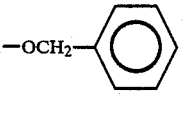 | —OH | 1760 | 1745 | (CDCl$_3$) 6.2 to 7.7 ppm,m,12H + exchangeable 1H 4.9 ppm,s,2H; 3.4 ppm,AB,2H |

TABLE I-continued

| Ex. | R₁ | R | R₂ | IR(cm⁻¹) $\nu$C=O lactone | $\nu$C=O extra-cyclic | NMR (solvent) |
|---|---|---|---|---|---|---|
| 8 | 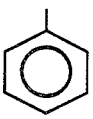 | —O—C₂H₅ | Cl | 1770 | 1730 | (CDCl₃)<br>6.6 to 7.8 ppm,m,8H;<br>4 ppm,q,2H;<br>3.5 ppm,AB,2H; 1.1 ppm,t,3H |
| 9 | 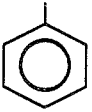 | 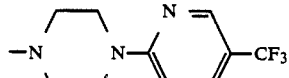 | Cl | 1805 | 1640 | (DMSO—d₆)<br>8.3 ppm,d,1H;<br>6.6 to 7.8 ppm,m,10H;<br>3.7 ppm,AB,2H; 3.6 ppm,m,4H;<br>3.4 ppm,m,4H |
| 10 | 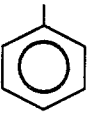 | 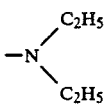 | Cl | 1805 | 1635 | (CDCl₃)<br>6.8 to 7.5 ppm,m,8H;<br>2.8 to 3.8 ppm,m,<br>6H; 1.2 ppm,t,3H; 1.1 ppm,t,3H |
| 11 |  | 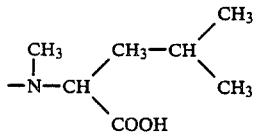 | Cl | 1815 | 1640 (amide)<br>1710 (acid) | (CDCl₃ + DMSO—d₆)<br>6.7 to 7.8 ppm,m,8H +<br>exchangeable 1H<br>4.8 ppm,m,1H; 3.7 ppm,m,2H;<br>2.9 ppm,s,3H; 1.5 ppm,m,3H;<br>0.9 ppm,m,6H |
| 12 |  | 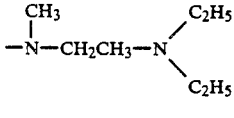 | —Cl | 1805 | 1640 | (DMSO—d₆)<br>10.5 ppm,m, exchangeable 1H<br>7.9 ppm,d,1H;<br>7 to 7.7 ppm,m,7H;<br>3.8 ppm,AB,2H; 3.4 ppm,m,2H;<br>3.1 ppm,s,3H; 3 ppm,m,6H;<br>1.3 ppm,t,3H; 1.2 ppm,t,3H |
| 13 | 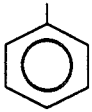 | 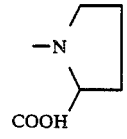 | —Cl | 1815 | 1640 (amide)<br>1720 (acid) | (CD₃OD)<br>7.1 to 7.9 ppm,m,8H;<br>4.3 ppm,m,1H;<br>3.7 ppm,s,2H; 3.6 ppm,m,2H;<br>2.1 ppm,m,4H |
| 14 |  | 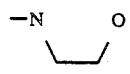 | —Cl | 1810 | 1640 | (CDCl₃ + DMSO—d₆)<br>6.5 to 7.6 ppm,m,8H;<br>3.5 ppm,m,10H |
| 15 | 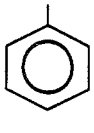 | 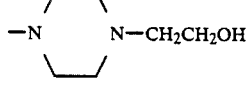 | —Cl | 1810 | 1645 | (DMSO—d₆)<br>7.7 ppm,d,1H;<br>7.3 to 7.6 ppm,m,7H;<br>2.8 to 4.5 ppm,m,14H +<br>exchangeable 1H |
| 16 | 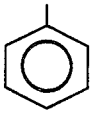 | 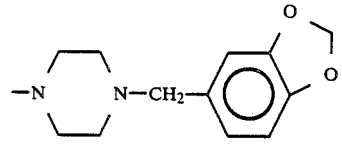 | —Cl | 1815 | 1640 | (DMSO—d₆)<br>11.8 ppm,m, exchangeable 1H<br>7.7 ppm,d,1H;<br>6.7 to 7.5 ppm,m,10H;<br>6 ppm,s,2H;<br>2.6 to 4.5 ppm,m,12H |
| 17 |  | 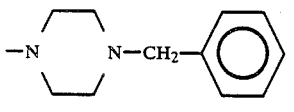 | —Cl | 1795 | 1645 | (CDCl₃)<br>6.7 to 7.6 ppm,m,13H;<br>3.1 to 3.7 ppm,m,8H;<br>2.1 to 2.6 ppm,m,4H |

TABLE I-continued

| Ex. | R₁ | R | R₂ | IR(cm⁻¹) $vC=O$ lactone | IR(cm⁻¹) $vC=O$ extra-cyclic | NMR (solvent) |
|---|---|---|---|---|---|---|
| 18 | phenyl | $-N\underset{\phantom{x}}{\diagup\!\!\!\diagdown}N-$(3-CF₃-phenyl) (piperazinyl) | $-Cl$ | 1795 | 1645 | (DMSO—d₆) 6.8 to 7.9 ppm,m,12H; 5.6 ppm,s, exchangeable 1H 3.9 ppm,AB,2H; 2.8 to 3.9 ppm,m,8H |
| 19 | phenyl | piperazinyl-(3-CH₃-phenyl) | $-Cl$ | 1815 | 1650 | (DMSO—d₆) 5.6 to 7.8 ppm,m,12H + exchangeable 1H 3 to 4.2 ppm,m,10H |
| 20 | phenyl | piperazinyl-CH₂-(3,4-methylenedioxyphenyl) | $-F$ | 1800 | 1640 | (CDCl₃ + DMSO—d₆) 12.7 ppm,m, exchangeable 1H 6.5 to 7.8 ppm,m,11H; 6 ppm,s,2H; 2.8 to 4.5 ppm,m,12H |
| 21 | phenyl | $-N(CH_3)-CH_2-COOH$ | $-H$ | 1810 | 1655 (amide) 1725 (acid) | (DMSO—d₆) 7 to 7.7 ppm,m,9H + exchangeable 1H 3.3 to 4 ppm,m,4H; 3.1 ppm,s, and 2.7 ppm,s,3H |
| 22 | phenyl | piperazinyl-CH₂-(3,4-methylenedioxyphenyl) | $-H$ | 1795 | 1650 | (CDCl₃) 6.5 to 7.7 ppm,m,12H; 5.9 ppm,s,2H; 3.2 to 3.6 ppm,m,8H; 2.1 to 2.6 ppm,m,4H |
| 23 | $-H$ | piperazinyl-CH₂-(3,4-methylenedioxyphenyl) | $-H$ | 1805 | 1645 | (CDCl₃) 6.3 to 7.7 ppm,m,7H; 5.9 ppm,s,2H; 4.1 ppm, d d,1H; 2.6 to 3.8 ppm,m,8H; 2.1 to 2.6 ppm,m,4H |
| 24 | $-H$ | morpholino | $-H$ | 1810 | 1640 | (CDCl₃) 6.7 to 7.5 ppm,m,4H; 4.1 ppm,d d,1H; 3.2 to 3.8 ppm,m,8H; 3 ppm,m,2H |
| 25 | $-H$ | piperazinyl-CH₂-(3-CH₃-phenyl) | $-H$ | 1810 | 1650 | (CDCl₃) 6.3 to 7.7 ppm,m,8H; 4.1 ppm,d d,1H; 2.7 to 3.9 ppm,m,10H; 2.3 ppm,s,3H |
| 26 | $-H$ | piperazinyl-(3-CH₃-phenyl) | $-Cl$ | 1810 | 1650 | (CDCl₃ + CF₃CO₂H) 6.7 to 7.7 ppm,m,7H; 4.2 ppm,m,5H; 3.7 ppm,m,4H; 3.3 ppm,d,2H; 2.4 ppm,s,3H |
| 27 | phenyl | piperazinyl-(4-CF₃-pyridin-2-yl) | $-Cl$ | 1810 | 1640 | (DMSO—d₆) 8.5 ppm,d,1H; 6.85 to 7.7 ppm,m,10H; 3.3 to 4 ppm,m,10H |

TABLE I-continued

| Ex. | $R_1$ | R | $R_2$ | IR(cm$^{-1}$) $\nu C=O$ lactone | $\nu C=O$ extra-cyclic | NMR (solvent) |
|---|---|---|---|---|---|---|
| 28 | phenyl | −N(CH$_3$)−CH(COOH)−CH$_2$−phenyl | −Cl | 1800 | 1640 (amide) 1720 (acid) | (CDCl$_3$) 6.9 to 7.5 ppm,m,13H; 5.25 ppm,m, exchangeable 1H 2.7 to 3.4 ppm,m,5H; 2.8 ppm,s,3H |
| 29 | phenyl | −N(piperazine)N−CH$_2$−COOH | −Cl | 1815 | 1645 (amide) 1750 (acid) | (DMSO−d$_6$) 6.8 to 7.8 ppm,m,8H; 6.5 to 4.5 ppm,m, exchangeable 2H 3 to 4.3 ppm,m,12H |
| 30 | phenyl | −N(piperidinyl with 3-methoxyphenyl) | −Cl | 1795 | 1635 | (CDCl$_3$ + DMSO−d$_6$) 7.2 to 8 ppm,m,8H; 6.6 to 7 ppm,m,4H; 3.5 to 4.2 ppm,m,4H; 3.75 ppm,s,3H; 3.7 ppm,s,2H; 2.6 to 3.4 ppm,m,1H; 1.4 to 2.1 ppm,m,4H |
| 31 | phenyl | −N(CH$_3$)−CH$_2$−(isochroman-like) | −Cl | 1800 | 1655 | (CDCl$_3$) 7 to 7.5 ppm,m,12H; 4.7 to 5.1 ppm,m,1H; 3.5 to 4.5 ppm,m,2H; 3.3 to 3.8 ppm,m,2H; 3.1 ppm,s,3H; 2.6 to 2.9 ppm,m,4H |
| 32 | phenyl | −N(CH$_3$)−CH$_2$−(1-ethylpyrrolidin-2-yl) | −Cl | 1810 | 1645 | (DMSO−d$_6$) 9.5 to 10.3 ppm,m, exchangeable 1H 7 to 7.8 ppm,m,8H; 2.8 to 4.3 ppm,m,12H; 1.5 to 2.3 ppm,m,4H; 1 to 1.5 ppm,m,3H |
| 33 | phenyl | −N(piperazine)N−(4-fluorophenyl) | −CH$_3$ | 1800 | 1655 | (CDCl$_3$) 6.7 to 7.7 ppm,m,12H; 3.5 to 3.8 ppm,m,4H; 3.55 ppm,s,2H; 2.8 to 3.2 ppm,m,4H; 2.4 ppm,s,3H |
| 34 | −CH$_3$−CH$_3$−CH$_3$ | −N(piperazine)N−CH$_2$−(benzodioxol-5-yl) | −H | 1800 | 1640 | (DMSO−d$_6$) 7 to 7.6 ppm,m,exchangeable 1H 6.8 to 7.5 ppm,m,7H; 6.1 ppm,s,2H; 2.8 to 4.4 ppm,m,12H; 1.5 to 2 ppm,m,2H; 1 to 1.6 ppm,m,2H; 0.6 to 0.9 ppm,m,3H |
| 35 | 4-CH$_3$-phenyl | −N(CH$_3$)−CH$_2$−CH(CH$_3$)−N(C$_2$H$_5$)$_2$ | −Cl | 1805 | 1645 | (CDCl$_3$) 7.5 ppm,d,1H; 6.8 to 7.5 ppm,m,6H; 3.4 to 4.4 ppm,m,4H; 3.2 ppm,s,3H; 2.7 to 3.4 ppm,m,6H; 2.3 ppm,s,3H; 1.3 ppm,t,6H |

TABLE I-continued

| Ex. | R₁ | R | R₂ | IR(cm⁻¹) vC=0 lactone | vC=0 extra-cyclic | NMR (solvent) |
|---|---|---|---|---|---|---|
| 36 | CH₃—⟨phenyl⟩— | —N(CH₃)—CH₂—CH₂—N(CH₃)—CH₂—CH(CH₃)—N(CH(CH₃)₂)(CH₃) | —Cl | 1800 | 1645 | (CDCl₃) 10 to 10.5 ppm,m, exchangeable 1H 7 to 7.6 ppm,m,7H; 3.3 to 4.1 ppm,m,4H; 3.2 ppm,s,3H; 2.5 to 3.2 ppm,m,4H; 2.3 ppm,s,3H; 1 to 2 ppm,m,12H |
| 37 | CH₃—⟨phenyl⟩— | piperazine-N—CH₂CH₂OH | —Cl | 1805 | 1640 | (DMSO—d₆) 7.2 to 7.7 ppm,m,7H; 2.6 to 4.3 ppm,m,14H; 2.5 to 4 ppm,m, exchangeable 2H 2.3 ppm,s,3H |

PHARMACOLOGICAL STUDY

EXAMPLE 38

Acute hypoxia in mice

Male CD1 mice (Charles River) which have received intraperitoneally the test compound or a reference compound 30 minutes beforehand are subjected to an acute hypoxia of the hypobaric type. For this purpose, they are placed in an enclosure in which the atmospheric pressure can be rapidly lowered (in the space of 30 seconds) to a value of 160 mbar, which causes the death of all the animals approximately 15 seconds after this hypoxic pressure has been attained.

The survival of the brain is assessed by measuring the time at which the final respiratory gasp is observed.

The survival time of a treated batch is compared with that of a control batch receiving only the solvent.

The percentage increase in the survival time after the animals are treated with the compounds of the invention is shown in Table II. (Values underlined <0.05).

As seen in Table II, the compounds of the invention exert a potent antihypoxic effect, which is greatly superior to that of the reference compounds. In effect, at a dose of 100 mg/kg, meclofenoxate, pyritinol and piracetam increased the brain survival time of the animals by only 22%, 27% and 11%, respectively. The protection is significant only in the case of pyritinol.

At the same dose, the compounds of the invention have a protective effect which is 2 to 8 times as potent as the latter compound. The increase in the survival time is, for example, 100% for the compound of Examples 16 and 20, 126% for the compound of Example 22, greater than 130% for the compounds of Examples 15 and 26, and greater than 180% for the compounds of Examples 9 and 12.

TABLE II

| | Percentage increase in the survival time DOSES mg/kg (I.P.) | | | | | | | |
|---|---|---|---|---|---|---|---|---|
| COMPOUND | 3 | 10 | 30 | 100 | 200 | 300 | 600 | 1000 |
| Meclofenoxate | | | +4 | +22 | | | +190 | |
| Pyritinol | | | +13 | +27 | +77 | | | |
| Piracetam | | | | +11 | | | | +25 |
| Ex. 1 | | | | +46 | | | | |
| Ex. 2 | | | | +38 | | | | |
| Ex. 3 | | | | +29 | | | | |
| Ex. 4 | | | | +17 | | | | |
| Ex. 5 | | | | +69 | | | | |
| Ex. 6 | | | | +41 | | | | |
| Ex. 7 | | | | +14 | | +156 | | |
| Ex. 8 | | | | +52 | | | | |
| Ex. 9 | +65 | +82 | +77 | +183 | | | | |
| Ex. 10 | | | | +97 | | | | |
| Ex. 11 | | | | +159 | | | | |
| Ex. 12 | +32 | +41 | +84 | +185 | | | | |
| Ex. 13 | | | | +8 | | | | |
| Ex. 14 | | | | +88 | | | | |
| Ex. 15 | | +34 | +41 | +139 | +203 | | | |
| Ex. 16 | | | +64 | +100 | | | | |
| Ex. 17 | | | +40 | +66 | | | | |
| Ex. 18 | | +41 | +53 | +88 | | +103 | | |
| Ex. 19 | | | | +76 | | | | |
| Ex. 20 | | +52 | +104 | +100 | | +128 | | |
| Ex. 21 | | | | +14 | | | | |
| Ex. 22 | | +11 | +42 | +126 | | | | |
| Ex. 26 | | +52 | +53 | +135 | | +190 | | |
| Ex. 27 | | +36 | +59 | +76 | | | | |
| Ex. 28 | | | | +90 | | | | |
| Ex. 29 | | | +32 | +66 | | | | |
| Ex. 30 | | +32 | +36 | +103 | | | | |

TABLE II-continued

| | Percentage increase in the survival time | | | | | | | |
|---|---|---|---|---|---|---|---|---|
| | DOSES mg/kg (I.P.) | | | | | | | |
| COMPOUND | 3 | 10 | 30 | 100 | 200 | 300 | 600 | 1000 |
| Ex. 32 | | | +26 | | | | | |

EXAMPLE 39

Acute hypoxia in rats

Male Fischer 344 rats (Charles River) which have received the test compound or a reference compound 30 minutes beforehand are subjected to a deficiency in the oxygen supply by being placed in a normobaric enclosure in which the composition of the circulating gaseous mixture may be changed accurately. Whereas the control rats breath a gaseous mixture containing 21% of oxygen and 79% of nitrogen, the rats subjected to hypoxia breath a mixture of 3% oxygen and 97% nitrogen for 2 minutes.

At the end of the hypoxic period, the animals are rapidly sacrificed by total immersion in liquid nitrogen. The frozen brain is removed and the energy-rich compounds (ATP, ADP, AMP) are extracted and assayed by the luciferin luminescence method.

The tissue energy content (EC) is calculated according to ATKINSON's formula:

$$EC = \frac{ATP + \frac{1}{2}ADP}{ATP + ADP + AMP}$$

The results of this study are shown in Table III.

In the control animals, hypoxia leads to a slump in the tissue ATP level (−74.2%) which is accompanied by a rise in the mono- and diphosphate compounds (AMP, ADP). This is reflected in the fall in the total energy content (−25.3%).

At a dose of 300 mg/kg, piracetam exerts only very little protection, inhibiting by only 3.9% the effects of hypoxia on the ATP level.

At the same dose, meclofenoxate inhibits by 59.7% and 69.6%, respectively, the effects of hypoxia on the ATP level and the energy content. Such an effect is observed with a dose of 100 mg/kg or 30 mg/kg of compounds of the invention.

Under the same conditions, pyritinol at a dose of 100 mg/kg exerts only a more modest effect. The fall in ATP is inhibited by 23% while that in the energy content is inhibited by 35%. It is necessary to administer the high dose of 300 mg/kg in order to observe a distinct antihypoxic effect.

TABLE III

| ACUTE HYPOXIA IN RATS | | | |
|---|---|---|---|
| Control rats in normoxia | ATP = 2.373 μmol/g | EC = 0.959 | |
| Control rats in hypoxia | ATP = −74.2% | EC = −25.3% | |
| | DOSE mg/kg | % INHIBITION OF THE EFFECTS OF HYPOXIA | |
| COMPOUND | I.P. | ATP | EC |
| Meclofenoxate | 300 | 59.7 | 69.6 |
| Pyritinol | 030 | 11.1 | 16.6 |
| | 100 | 23.3 | 35.2 |
| | 300 | 90.4 | 85.4 |
| Piracetam | 300 | 3.9 | 1.6 |
| Example 1 | 100 | 54 | 61.7 |
| Example 9 | 030 | 65.6 | 60.1 |
| Example 16 | 100 | 77.5 | 76.3 |
| Example 20 | 030 | 56.9 | 61.3 |
| | 100 | 70.2 | 71.5 |

TABLE III-continued

| ACUTE HYPOXIA IN RATS | | | |
|---|---|---|---|
| Control rats in normoxia | ATP = 2.373 μmol/g | EC = 0.959 | |
| Control rats in hypoxia | ATP = −74.2% | EC = −25.3% | |
| | DOSE mg/kg | % INHIBITION OF THE EFFECTS OF HYPOXIA | |
| COMPOUND | I.P. | ATP | EC |
| Example 25 | 100 | 50.5 | 52.6 |

PHARMACEUTICAL PREPARATION

EXAMPLE 40

Gelatin capsules containing a 20-mg dose of 2-(2,3-dihydro-5-fluoro-2-oxo-3-phenyl-3-benzofuranyl)-1-[4-(3,4-methylenedioxybenzyl)piperazinyl]-1-oxoethane hydrochloride

| | |
|---|---|
| 2-(2,3-Dihydro-5-fluoro-2-oxo-3-phenyl-3-benzofuranyl)-1-[4-(3,4-methylenedioxybenzyl)piperazinyl]-1-oxoethane hydrochloride | 20 mg |
| Corn starch | 15 mg |
| Lactose | 25 mg |
| Talc | 5 mg |
| For a No. 3 gelatin capsule. | |

We claim:

1. Compounds of general formula I $$\text{(structure with } R_2 \text{ on benzofuran ring, } R_1 \text{ and CH}_2\text{COR substituents)} \tag{I}$$

in which:
  $R_1$ denotes a hydrogen atom, a linear or branched alkyl radical having 1 to 4 carbon atoms or a phenyl radical optionally substituted with a halogen atom or with an alkoxy radical having 1 to 4 carbon atoms or an alkyl radical having 1 to 4 carbon atoms,
  $R_2$ denotes a hydrogen or halogen atom, a hydroxyl radical, an alkyl radical having 1 to 4 carbon atoms or an alkoxy radical containing 1 to 4 carbon atoms,
  R denotes a radical of general formula A $$-N\diagup^{X}_{\diagdown Y} \tag{A}$$

in which x and y form, together with the nitrogen to which they are attached, a 1-piperazinyl radical (optionally substituted at the 4-position with a hydroxyalkyl radical having 1 to 4 carbon atoms, a carboxyalkyl radical having 2 to 5 carbon atoms, a benzyl radical optionally substituted with an alkyl radical having 1 to 4 carbon atoms, a 3,4-methylenedioxybenzyl radical, a phenyl radical optionally substituted with an alkyl radical having 1 to 4 carbon atoms or with a trifluoromethyl radical or with a halogen atom, or a 2-pyridyl radical optionally substituted with an alkyl radical having 1 to 4 carbon atoms or with a trifluoromethyl radical), in racemic form or in the form of an optical isomer, or an addition salt thereof with a pharmaceutically-acceptable inorganic or organic acid when it contains a salifiable basic group, or an addition salt thereof with a pharmaceutically-acceptable inorganic or organic base when it contains a salifiable acidic group.

2. A compound of claim 1 in which $R_2$ denotes a halogen atom, in racemic form or in the form of optical isomers, and their addition salts with a pharmaceutically acceptable inorganic or organic acid when they contain a salifiable basic group, or their addition salts with a pharmaceutically acceptable inorganic or organic base when they contain a salifiable acidic group.

3. Compound of claim 1 being 2-(5-Fluoro-2,3-dihydro-2-oxo-3-phenyl-3-benzofuranyl)-1-[4-(3,4-methylenedioxybenzyl)piperazinyl]-1-oxoethane and its addition salts with a pharmaceutically acceptable acid.

4. Compound of claim 1 being 2-(5-Chloro-2,3-dihydro-2-oxo-3-phenyl-3-benzofuranyl)-1-[4-(5-trifluoromethyl-2-pyridyl)piperazinyl]-1-oxoethane and its addition salts with a pharmaceutically acceptable acid.

5. Compound of claim 1 being 2-(5-chloro-2,3-dihydro-2-oxo-3-phenyl-3-benzofuranyl)-1-[4-(2-hydroxyethyl)piperazinyl]-1-oxoethane and its addition salts with a pharmaceutically-acceptable acid.

6. Compound of claim 1 being 2-(2,3-dihydro-2-oxo-3-propyl-3-benzofuranyl)-1-[4-(3,4-methylenedioxybenzyl)piperazinyl]-1-oxoethane and its addition salts with a pharmaceutically-acceptable acid.

7. A method of treating a disease linked to hypoxemia and the energy insufficiency or cerebral aging in a subject suffering therefrom comprising the step of administering to the said subject an amount of a compound of claim 1 which is effective for the alleviation of such disease.

8. A pharmaceutical composition suitable for use in the treatment of a disease linked to hypoxemia and to energy insufficiency or cerebral aging comprising as active ingredient an amount of a compound of claim 1 which is effective for said purpose, in combination or as a mixture with a pharmaceutically-acceptable non-toxic inert vehicle or excipient.

* * * * *

UNITED STATES PATENT AND TRADEMARK OFFICE
CERTIFICATE OF CORRECTION

PATENT NO. : 4,885,299

DATED : December 5, 1989

INVENTOR(S) : Gilbert Lavielle, Jean Lepagnol

It is certified that error appears in the above-identified patent and that said Letters Patent is hereby corrected as shown below:

```
Column 1, line 50; "radical or"   should read -- radical, or --.
Column 3, line 42; "Icforms"   should read -- Ic forms --.
Column 9, line 4/5;"1oxoethane"   should read -- 1-oxoethane --.
Column 9, line 54; "a"   should read -- at --.
Column 11, line 57/58;"-oxoethanehydrochloride"  should read
    -- -oxoethane hydrochloride --.
Column 11, line 64; "-2oxo-"   should read -- -2-oxo- --
Column 12, line 8/9; "-oxoethanehydrochloride"   should read
    -- -oxoethane hydrochloride --
Column 14, line 13; "(2-hydroethyl)"   should read
    -- (2-hydroxyethyl) --.
Column 13/14, Table I, Example 1, last column, 3rd line;
    -- ",H;"   should read --  -- ,8H; --.
Title Page, Abstract, column 2, last line; "-piperazinly"
    should read --  -piperazinyl --.
```

Signed and Sealed this

Thirteenth Day of November, 1990

Attest:

HARRY F. MANBECK, JR.

Attesting Officer

Commissioner of Patents and Trademarks